(12) United States Patent
Umeda et al.

(10) Patent No.: US 8,686,006 B2
(45) Date of Patent: Apr. 1, 2014

(54) PHARMACEUTICAL COMPOSITION FOR IMPROVING INTESTINAL ABSORPTION

(75) Inventors: Masayuki Umeda, Ikoma (JP); Akio Kimura, Ikoma (JP); Kenji Ueda, Ikoma (JP); Koji Sakanaka, Ikoma (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 107 days.

(21) Appl. No.: 13/124,797

(22) PCT Filed: Oct. 22, 2009

(86) PCT No.: PCT/JP2009/068164
§ 371 (c)(1),
(2), (4) Date: Apr. 18, 2011

(87) PCT Pub. No.: WO2010/047361
PCT Pub. Date: Apr. 29, 2010

(65) Prior Publication Data
US 2011/0201655 A1    Aug. 18, 2011

(30) Foreign Application Priority Data

Oct. 22, 2008    (JP) .................................. 2008-271948

(51) Int. Cl.
*A61K 31/44*    (2006.01)
(52) U.S. Cl.
USPC ......................................................... 514/357
(58) Field of Classification Search
USPC ......................................................... 514/357
See application file for complete search history.

(56) References Cited

U.S. PATENT DOCUMENTS

| | | |
|---|---|---|
| 5,645,856 A | 7/1997 | Lacy et al. |
| 2003/0032623 A1 | 2/2003 | Ban et al. |
| 2005/0014800 A1 | 1/2005 | Matsuoka et al. |
| 2007/0092560 A1* | 4/2007 | Sukuru .......................... 424/451 |
| 2008/0161270 A1* | 7/2008 | Matsuoka et al. .............. 514/63 |

FOREIGN PATENT DOCUMENTS

| | | |
|---|---|---|
| EP | 1 457 205 A1 | 9/2004 |
| JP | 2005-336174 A | 12/2005 |
| WO | WO 97/40823 A1 | 11/1997 |
| WO | WO 2005/102331 A1 | 11/2005 |
| WO | WO 2006/035759 A1 | 4/2006 |
| WO | WO 2006/035760 A1 | 4/2006 |
| WO | WO 2006/043518 A1 | 4/2006 |

OTHER PUBLICATIONS

Supplementary European Search Report mailed Apr. 24, 2013 for EP 09 82 2058.
Murai, Masaaki et al., "SA13353 (1-[2-(1-adamantyl)ethyl]-1-pentyl-3-[3-(4-pyridyl)propyl]urea) inhibits TNF-αproduction through the activation of capsaicin-sensitive afferent neurons mediated via transient receptor potential vanilloid 1 in vivo", *European Journal of Pharmacology*, 588(2-3), (2008), 309-315.

* cited by examiner

*Primary Examiner* — Paul Zarek
(74) *Attorney, Agent, or Firm* — Holtz Holtz Goodman & Chick PC

(57) ABSTRACT

An object of the present invention is to provide a pharmaceutical composition that improves intestinal absorption of a compound having a structure represented by the general formula [1]. The composition containing a compound represented by the general formula [1] or a salt thereof and (b) a lipophilic substance improves intestinal absorption of the compound. In the formula, A represents —($NR^4$)—, —($CR^5R^6$)— or the like; B represents an alkylene group or an alkenylene group; $R^1$ represents an alkyl group, an alkenyl group or the like; $R^2$ represents an adamantylalkyl group or the like; $R^3$ represents an unsaturated heterocyclic ring; $R^4$, $R^5$ and $R^6$ each represent a hydrogen atom or the like; and X represents an oxygen atom or the like.

[1]

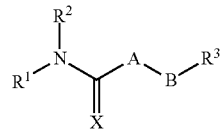

4 Claims, No Drawings

PHARMACEUTICAL COMPOSITION FOR IMPROVING INTESTINAL ABSORPTION

This application is the United States national phase application of International Application PCT/JP2009/068164 filed Oct. 22, 2009.

TECHNICAL FIELD

The present invention relates to a pharmaceutical composition containing (a) a compound represented by the following general formula [1] or a salt thereof (which may be hereinafter generically referred to as a "subject compound") and (b) a lipophilic substance:

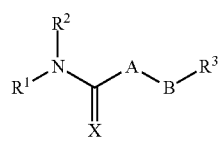

[1]

wherein A represents —(NR$^4$)—, —(CR$^5$R$^6$)— or —O—; B represents an alkylene group or an alkenylene group, which may contain in the chain thereof —O—, —S—, —(NR$^7$)—, —CO—, —N= or

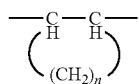

in which the alkylene group and the alkenylene group each may be substituted with a hydroxy group, an alkoxy group, an aryl group, a siloxy group or a saturated or unsaturated heterocyclic ring, and each may be bonded to A to form a saturated heterocyclic ring; R$^1$ represents a hydrogen atom, an alkyl group, an alkenyl group, an alkynyl group, a cycloalkyl group, a cycloalkenyl group, a hydroxy group or an amino group, in which the alkyl group, the alkenyl group, the alkynyl group, the cycloalkyl group and the cycloalkenyl group each may be substituted with a halogen atom, a hydroxy group, an amino group, a cycloalkyl group, an aryl group, a carboxyl group, an alkoxycarbonyl group, an aminocarbonyl group, an adamantyl group, an aryloxycarbonyl group, a cyano group or a saturated or unsaturated heterocyclic ring, and each hydrogen atom of the amino group, the hydroxy group and the aminocarbonyl group may be replaced by an alkyl group, a cycloalkyl group, an aryl group, an arylalkyl group, an acyl group, an alkoxycarbonyl group, a cycloalkyloxycarbonyl group, an arylalkoxycarbonyl group, a halogenoalkoxycarbonyl group, an unsaturated heterocyclic ring or an alkyl group substituted with an unsaturated heterocyclic ring; R$^2$ represents an adamantylalkyl group, an adamantyloxyalkyl group, an adamantylaminoalkyl group or an adamantylaminocarbonylalkyl group; R$^3$ represents an unsaturated heterocyclic ring; R$^4$ represents a hydrogen atom, an alkyl group, an adamantylalkyl group, a carboxyalkyl group, an alkoxycarbonyl group, an alkoxycarbonylalkyl group, an amino group, an alkylamino group, an acylamino group or an alkoxycarbonylamino group; R$^5$ and R$^6$, which are the same or different, each represents a hydrogen atom, an alkyl group, an amino group or an alkoxycarbonylamino group; R$^7$ represents a hydrogen atom or an alkyl group; X represents an oxygen atom or a sulfur atom; and n represents an integer of from 1 to 5.

BACKGROUND ART

The subject compound is disclosed along with the production method thereof in Patent Document 1 (JP-A-2002-53555), and has an inhibitory activity against TNF-α (tumor necrosis factor α) formation. Accordingly, it is suggested that the subject compound may be a therapeutic agent for autoimmune disease, such as chronic rheumatoid arthritis, allergy and diabetes (JP-A-2002-53555).

The subject compound has an angiogenesis inhibitory activity, and it is suggested that the compound may be a therapeutic agent for diabetic retinopathy, retinopathy of prematurity, macular degeneration, neovascular glaucoma, retinal vein occlusion, retinal artery occlusion, pterygium, rubeosis, corneal vascularization and the like (JP-A-2003-226686). Furthermore, it is suggested that the subject compound may be a therapeutic agent for osteoporosis, osteoarthrosis, respiratory disease, skin disease, neurodegenerative disease and the like (JP-A-2005-336173, JP-A-2005-336174, JP-A-2006-117654, JP-A-2006-117653 and JP-A-2006-143707). As described above, the subject compound is clinically very useful compound.

On the other hand, the subject compound is low in intestinal absorption on oral administration, and there are some cases where sufficient drug efficacy may not be obtained by oral administration. However, there has been no report investigating a pharmaceutical formulation that improves the intestinal absorption of the subject compound, and it has completely not been apparent as to which composition improves the intestinal absorption of the subject compound.

DISCLOSURE OF THE INVENTION

Problems to be Solved by the Invention

An object of the invention is to provide a pharmaceutical composition that improves the intestinal absorption of the subject compound.

Means for Solving the Problems

As a result of earnest investigations made by the present inventors for exploring a pharmaceutical composition that improves the intestinal absorption of the subject compound, it has been found that the intestinal absorption of the subject compound is improved by dissolving the subject compound in a lipophilic substance.

Accordingly, the invention relates to a pharmaceutical composition comprising (a) a compound represented by the following general formula [1] or a salt thereof and (b) a lipophilic substance:

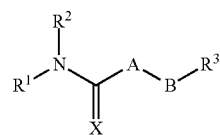

[1]

wherein A represents —(NR$^4$)—, —(CR$^5$R$^6$)— or —O—; B represents an alkylene group or an alkenylene group, which may contain in the chain thereof —O—, —S—, —(NR$^7$)—, —CO—, —N= or

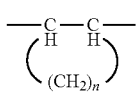

in which the alkylene group and the alkenylene group each may be substituted with a hydroxy group, an alkoxy group, an aryl group, a siloxy group or a saturated or unsaturated heterocyclic ring, and each may be bonded to A to form a saturated heterocyclic ring; $R^1$ represents a hydrogen atom, an alkyl group, an alkenyl group, an alkynyl group, a cycloalkyl group, a cycloalkenyl group, a hydroxy group or an amino group, in which the alkyl group, the alkenyl group, the alkynyl group, the cycloalkyl group and the cycloalkenyl group each may be substituted with a halogen atom, a hydroxy group, an amino group, a cycloalkyl group, an aryl group, a carboxyl group, an alkoxycarbonyl group, an aminocarbonyl group, an adamantyl group, an aryloxycarbonyl group, a cyano group or a saturated or unsaturated heterocyclic ring, and each hydrogen atom of the amino group, the hydroxy group and the aminocarbonyl group may be replaced by an alkyl group, a cycloalkyl group, an aryl group, an arylalkyl group, an acyl group, an alkoxycarbonyl group, a cycloalkyloxycarbonyl group, an arylalkoxycarbonyl group, a halogenoalkoxycarbonyl group, an unsaturated heterocyclic ring or an alkyl group substituted with an unsaturated heterocyclic ring; $R^2$ represents an adamantylalkyl group, an adamantyloxyalkyl group, an adamantylaminoalkyl group or an adamantylaminocarbonylalkyl group; $R^3$ represents an unsaturated heterocyclic ring; $R^4$ represents a hydrogen atom, an alkyl group, an adamantylalkyl group, a carboxyalkyl group, an alkoxycarbonyl group, an alkoxycarbonylalkyl group, an amino group, an alkylamino group, an acylamino group or an alkoxycarbonylamino group; $R^5$ and $R^6$, which are the same or different, each represents a hydrogen atom, an alkyl group, an amino group or an alkoxycarbonylamino group; $R^7$ represents a hydrogen atom or an alkyl group; X represents an oxygen atom or a sulfur atom; and n represents an integer of from 1 to 5.

The invention relates to, as another embodiment, a pharmaceutical composition comprising (a) at least one compound selected from the following group or a salt thereof and (b) a lipophilic substance:

1-[2-(1-adamantyl)ethyl]-1-pentyl-3-[3-(4-pyridyl)propyl]urea,

1-[2-(1-adamantyl)ethyl]-3-[3-(4-pyridyl)propyl]-1-(3,3,3-trifluoropropyl)urea,

1-[2-(1-adamantyl)ethyl]-1-(2-butenyl)-3-[3-(4-pyridyl)propyl]urea,

1-[2-(1-adamantyl)ethyl]-1-[2-[N-(t-butoxycarbonyl)-N-methylamino]ethyl]-3-[3-(4-pyridyl)propyl]urea, 1-[3-(1-adamantyl)propyl]-1-propyl-3-[3-(4-pyridyl)propyl]urea, (Z)-1-[2-(1-adamantyl)ethyl]-1-pentyl-3-[3-(4-pyridyl)-2-propenyl]urea, (−)-1-[2-(1-adamantyl)ethyl]-3-[2-methyl-3-(4-pyridyl)propyl]-1-pentylurea, 1-[2-(1-adamantyl)ethyl]-3-[1-methyl-3-(4-pyridyl)propyl]-1-pentylurea, (+)-1-[2-(1-adamantyl)ethyl]-1-[2-[N-(t-butoxycarbonyl)-N-methylamino]ethyl]-3-[(2-methyl-3-(4-pyridyl)propyl]urea, 5-(4-pyridyl)valeric acid N-[2-(1-adamantyl)ethyl]-N-pentylamide, 3-(4-pyridylmethylthio)propionic acid N-[2-(1-adamantyl)ethyl]-N-pentylamide, 2-[2-(4-pyridyl)ethylthio]acetic acid N-(2-(1-adamantyl)ethyl)-N-pentylamide, 6-(4-pyridyl)caproic acid N-[2-(1-adamantyl)ethyl]-N-pentylamide, cis-1-[2-(1-adamantyl)ethyl]-1-pentyl-3-[2-(4-pyridyl)cyclopropylmethyl]urea, 1-[2-(1-adamantyl)ethyl]-3-[2-methyl-3-(4-pyridyl)propyl]-1-pentylurea, 1-[2-(1-adamantyl)ethyl]-1-[2-[N-(t-butoxycarbonyl)-N-methylamino]ethyl]-3-[2-methyl-3-(4-pyridyl)propyl]urea, (E)-1-[2-(1-adamantyl)ethyl]-1-pentyl-3-[3-(4-pyridyl)-2-propenyl]urea and (+)-1-[2-(1-adamantyl)ethyl]-3-[2-methyl-3-(4-pyridyl)propyl]-1-pentylurea.

The invention relates to, as still another embodiment, a pharmaceutical composition comprising (a) the subject compound and (b) a propylene glycol fatty acid ester and/or a glycerin fatty acid ester.

The invention relates to, as still another embodiment, a pharmaceutical composition comprising (a) the subject compound, (b) a propylene glycol fatty acid ester and/or a glycerin fatty acid ester, and (c) a solubilizer and/or a surfactant.

Advantageous Effects of the Invention

Upon injection of a solution containing the subject compound dissolved in a lipophilic substance into a duodenum or a jejunum of a rat, favorable entry of the compound into the blood is confirmed, as described later. Accordingly, the invention provides a pharmaceutical composition that improves the intestinal absorption of the subject compound.

MODE FOR CARRYING OUT THE INVENTION

The definitions of the terms (such as the atom, the group and the ring) referred herein will be described in detail below. In the case where the definition is applied, the preferred range and the like thereof are also inclusively applied.

The alkylene group includes a linear or branched alkylene group having from 1 to 12 carbon atoms, such as a methylene group, an ethylene group, a trimethylene group, a propylene group, a tetramethylene group, a pentamethylene group, a hexamethylene group, an octamethylene group, a decamethylene group, a dodecamethylene group, a methylmethylene group, an ethylethylene group, a dimethylethylene group, propylethylene group, an isopropylethylene group, a methyltrimethylene group, a 1-methylpropan-1,3-diyl group, a 2-methylpropan-1,3-diyl group and a butan-1,4-diyl group.

The alkenylene group includes a linear or branched alkenylene group having one or more double bond and having from 2 to 12 carbon atoms, such as a vinylene group, a propenylene group, a butenylene group, a pentenylene group, a hexenylene group, an octenylene group, a butanediylidene group and a methylpropenylene group.

The alkyl group represents a linear or branched alkyl group having from 1 to 12 carbon atoms, such as a methyl group, an ethyl group, a propyl group, a butyl group, a pentyl group, a hexyl group, an octyl group, a decyl group, a dodecyl group, an isopropyl group, an isobutyl group, an isopentyl group, an isohexyl group, an isooctyl group, a t-butyl group and a 3,3-dimethylbutyl group.

The alkoxy group represents a linear or branched alkoxy group having from 1 to 12 carbon atoms, such as a methoxy group, an ethoxy group, a propoxy group, a butoxy group, a hexyloxy group, an octyloxy group, a decyloxy group, a dodecyloxy group, an isopropoxy group and a t-butoxy group.

The alkenyl group represents a linear or branched alkenyl group having from 2 to 12 carbon atoms, such as a 1-propenyl group, an allyl group, an isopropenyl group, a 1-butenyl group, a 2-butenyl group, a 3-butenyl group, a 1-pentenyl group, a 2-pentenyl group, a 3-pentenyl group, a 4-pentenyl group and a 5-hexenyl group.

The alkynyl group represents a linear or branched alkynyl group having from 2 to 12 carbon atoms, such as an ethynyl group, a propynyl group and a butynyl group.

The cycloalkyl group represents a cycloalkyl group having from 3 to 20 carbon atoms, such as a cyclopropyl group, a cyclobutyl group, a cyclopentyl group, a cyclohexyl group, a cycloheptyl group, a cyclooctyl group, a cyclodecyl group and a cyclododecyl group.

The cycloalkenyl group represents a cycloalkenyl group having from 5 to 20 carbon atoms, such as a cyclopentenyl group, a cyclohexenyl group and a cycloheptenyl group.

The aryl group represents an aromatic hydrocarbon ring, such as a phenyl group and a naphthyl group, which may have one or more substituent, and examples of the substituent include an alkyl group, a cycloalkyl group, a carboxyl group, an amino group, a hydroxy group, an aminoalkyl group, a hydroxyalkyl group, a nitro group, a cyano group, a halogen atom and an alkyloxy group.

The siloxy group represents a silicon-containing organic group, such as a trialkylsilyloxy group, a dialkyl(aryl)silyloxy group and an alkyl(diaryl)silyloxy group and a triarylsilyloxy group.

The acyl group represents a hydrocarbonyl group, an alkylcarbonyl group, a cycloalkylcarbonyl group, an arylcarbonyl group or a heterocyclic carbonyl group. Specific examples thereof include a formyl group as a hydrocarbonyl group; an acetyl group, a propionyl group, a butylyl group, an isobutylyl group, a valeryl group, an isovaleryl group, a pivaloyl group, a monochloroacetyl group, a trifluoroacetyl group and the like, as an alkylcarbonyl group; a cyclopentylcarbonyl group, a cyclohexylcarbonyl group and the like, as a cycloalkylcarbonyl group; a benzoyl group, a naphthoyl group, a toluoyl group and the like, as an arylcarbonyl group; and a furoyl group, a thenoyl group, a picolinoyl group, a nicotinoyl group, an isonicotinoyl group, an imidazolylcarbonyl group and the like, as a heterocyclic carbonyl group.

The halogen atom represents fluorine, chlorine, bromine and iodine.

The heterocyclic ring represents a 5-membered to 20-membered saturated or unsaturated monocyclic heterocyclic ring or bicyclic heterocyclic ring containing from 1 to 4 atoms selected, for example, from a nitrogen atom, an oxygen atom and a sulfur atom, in which the heterocyclic ring may have one or more substituent, and examples of the substituent include an alkyl group, a cycloalkyl group, a carboxyl group, an amino group, a hydroxy group, an aminoalkyl group, a hydroxyalkyl group, a nitro group, a cyano group, a halogen atom, an alkyloxy group, an aryl group, an arylalkyl group and a saturated or unsaturated heterocyclic ring. When the heterocyclic ring has a nitrogen atom or a sulfur atom in the ring, the atom may be oxidized to form an N-oxide, an S-oxide and the like.

Specific examples of the saturated heterocyclic ring include a monocyclic heterocyclic ring, such as pyrrolidine, piperidine, homopiperidine and piperazine, each of which has a nitrogen atom in the ring, morpholine, which has a nitrogen atom and an oxygen atom in the ring, and thiomorpholine, which has a nitrogen atom and a sulfur atom in the ring, and the rings may be condensed with a benzene ring or the like to form a bicyclic heterocyclic ring, such as tetrahydroquinoline and tetrahydroisoquinoline.

Specific examples of the unsaturated heterocyclic ring include a monocyclic heterocyclic ring, such as pyrrole, pyridine, pyrazole, imidazole, pyrazine, pyridazine and pyrimidine, each of which has a nitrogen atom in the ring; a bicyclic heterocyclic ring, such as indole, quinoline, isoquinoline, benzimidazole, naphthyridine, pyrrolopyridine and imidazopyridine, each of which has a nitrogen atom in the ring; a monocyclic heterocyclic ring, such as furan, which has an oxygen atom in the ring; a bicyclic heterocyclic ring, such as benzofuran, which has an oxygen atom in the ring; a monocyclic heterocyclic ring, such as thiophene, which has a sulfur atom in the ring, a bicyclic heterocyclic ring, such as benzothiophene, which has a sulfur atom in the ring; a monocyclic heterocyclic ring, such as oxazole, isoxazole, thiazole and isothiazole, each of which has a nitrogen atom, an oxygen atom or a sulfur atom in the ring; and a bicyclic heterocyclic ring, such as benzoxazole, benzothiazole, thienopyridine, oxazolopyridine, thiazolopyridine and furopyridine, each of which has a nitrogen atom, an oxygen atom or a sulfur atom in the ring. The aforementioned unsaturated heterocyclic ring may have a structure that partially contains a saturated bond.

The salt in the invention is not particularly limited as far as the salt is a pharmaceutically acceptable salt, and examples thereof include a salt with an inorganic acid, such as hydrochloric acid, nitric acid, sulfuric acid and phosphoric acid, a salt with an organic acid, such as acetic acid, fumaric acid, maleic acid, succinic acid and tartaric acid, and a salt with an alkali metal or an alkaline earth metal, such as sodium, potassium and calcium. A quaternary ammonium salt of the subject compound is encompassed in the salt of the invention. In the case where there is a geometric isomer or an optical isomer of the subject compound, the isomers are encompassed in the scope of the invention. The subject compound may be in the form of a hydrate or a solvate.

Preferred examples of the subject compound include the following.

The compound, in which the groups defined in the general formula [1] each are selected from the following groups or each are a combination thereof, or a salt thereof.

(1) $R^2$: an adamantylalkyl group (2) $R^3$: a pyridine ring

In the compound, the compound, in which the groups defined in the general formula [1] each are the following groups, or a salt thereof is more preferred.

A: —(NR4)- or —($CR^5R^6$)—,

B: an alkylene group or an alkenylene group, which may contain in the chain —S— or

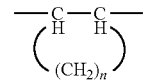

$R^1$: an alkyl group or an alkenyl group, in which the alkyl group and the alkenyl group each may be substituted with a halogen atom or an amino group, and the amino group may be substituted with an alkyl group, an acyl group, an alkoxycarbonyl group or a cycloalkyloxycarbonyl group, $R^2$: an adamantylalkyl group, $R^3$: a pyridine ring, $R^4$: a hydrogen atom, $R^5$ and $R^6$: a hydrogen atom, X: an oxygen atom, and n: 1.

In the compound, the compound, in which the groups defined in the general formula [1] each are the following groups, or a salt thereof is particularly preferred.

A: —NH— or a methylene group,

B: a propylene group, a 1-methylpropan-1,3-diyl group, a 2-methylpropan-1,3-diyl group, —CH$_2$—S—CH$_2$—, —S—CH$_2$—CH$_2$—, a butan-1,4-diyl group, a vinylene group, a propen-1,3-diyl group or

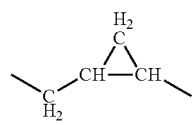

R$^1$: an ethyl group, a propyl group, a butyl group, pentyl group, a vinyl group, a 1-propenyl group, an allyl group, a 1-butenyl group, a 2-butenyl group, a 3-butenyl group, a 1-pentenyl group, a 2-pentenyl group, a 3-pentenyl group or a 4-pentenyl group, each of which may be substituted with a halogen atom or an amino group, and the amino group may be substituted with a methyl group and/or a t-butoxycarbonyl group, R$^2$: an adamantylethyl group or an adamantylpropyl group, R$^3$: a pyridine ring, and X: an oxygen atom.

Preferred specific examples of the subject compound include the following compounds and salts thereof.

1-[2-(1-adamantyl)ethyl]-1-pentyl-3-[3-(4-pyridyl)propyl]urea

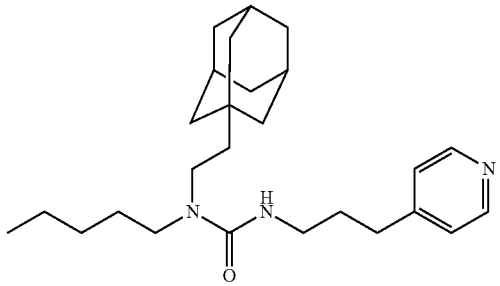 [SMILES: CCCCCN(CCC12CC3CC(CC(C3)C1)C2)C(=O)NCCCc1ccncc1]

1-[2-(1-adamantyl)ethyl]-3-[3-(4-pyridyl)propyl]-1-(3,3,3-trifluoropropyl)urea

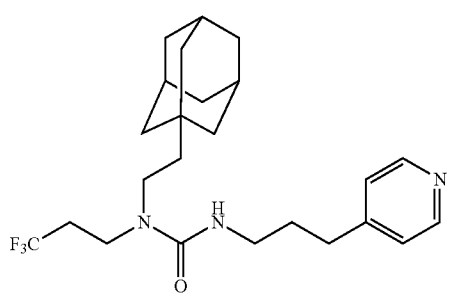 [SMILES: O=C(NCCCc1ccncc1)N(CCC(F)(F)F)CCC12CC3CC(CC(C3)C1)C2]

1-[2-(1-adamantyl)ethyl]-1-(2-butenyl)-3-[3-(4-pyridyl)propyl]urea

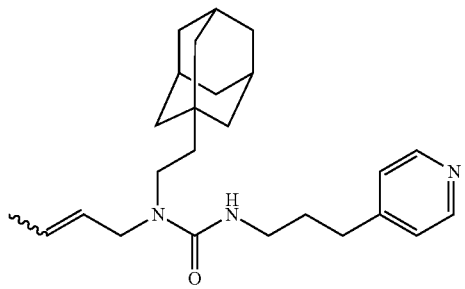

1-[2-(1-adamantyl)ethyl]-1-[2-[N-(t-butoxycarbonyl)-N-methylamino]ethyl]-3-[3-(4-pyridyl)propyl]urea

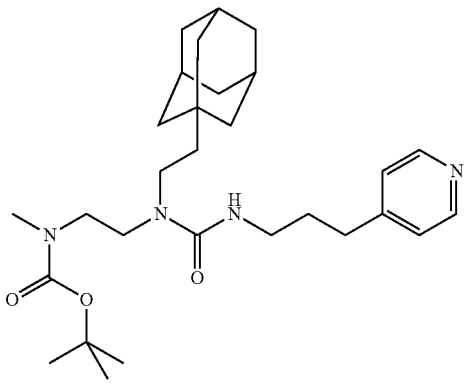 [SMILES: CN(CCN(CCC12CC3CC(CC(C3)C1)C2)C(=O)NCCCc1ccncc1)C(=O)OC(C)(C)C]

1-[3-(1-adamantyl)propyl]-1-propyl-3-[3-(4-pyridyl)propyl]urea

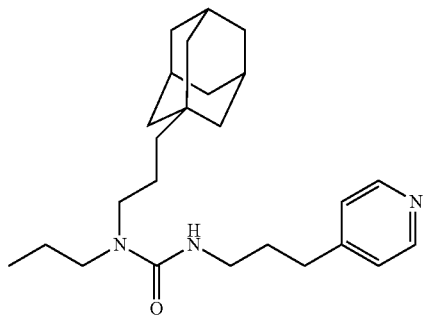 [SMILES: CCCN(CCCC12CC3CC(CC(C3)C1)C2)C(=O)NCCCc1ccncc1]

| 9 | 10 |
|---|---|
| (Z)-1-[2-(1-adamantyl)ethyl]-1-pentyl-3-[3-(4-pyridyl)-2-propenyl]urea | (+)-1-[2-(1-adamantyl)ethyl]-1-[2-[N-(t-butoxycarbonyl)-N-methylamino]ethyl]-3-[2-methyl-3-(4-pyridyl)propyl]urea |

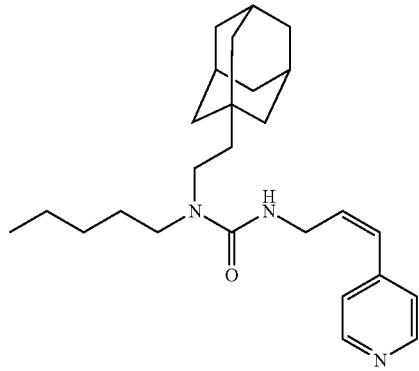 [SMILES: CCCCCN(CCC12CC3CC(CC(C3)C1)C2)C(=O)NC/C=C\c1ccncc1]

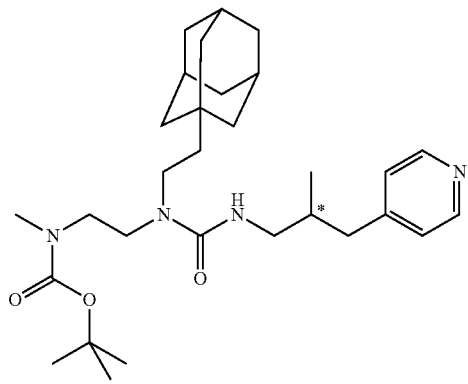

(−)-1-[2-(1-adamantyl)ethyl]-3-[2-methyl-3-(4-pyridyl)propyl]-1-pentylurea 5-(4-pyridyl)valeric acid N-[2-(1-adamantyl)ethyl]-N-pentylamide

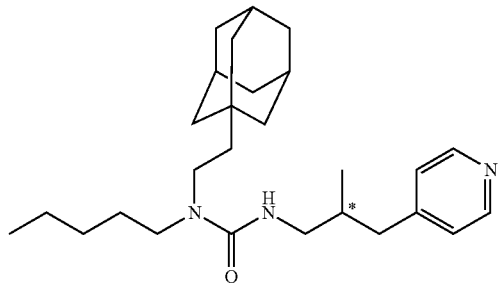 [SMILES: CCCCCN(CCC12CC3CC(CC(C3)C1)C2)C(=O)NCC(C)Cc1ccncc1]

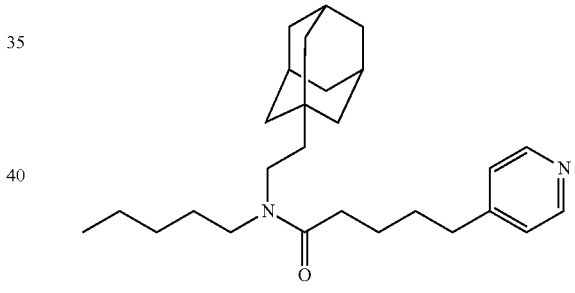

1-[2-(1-adamantyl)ethyl]-3-[1-methyl-3-(4-pyridyl)propyl]-1-pentylurea 3-(4-pyridylmethylthio)propionic acid N-[2-(1-adamantyl)ethyl]-N-pentylamide

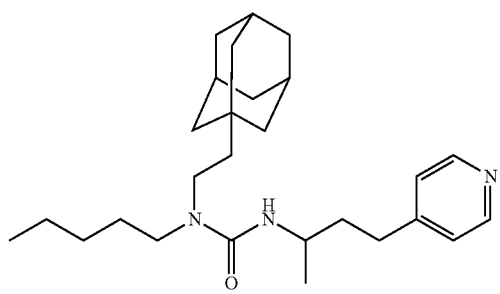 [SMILES: CCCCCN(CCC12CC3CC(CC(C3)C1)C2)C(=O)NC(C)CCc1ccncc1]

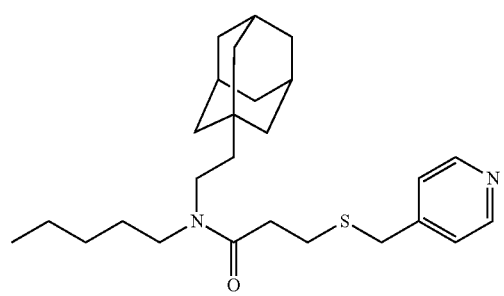 [SMILES: CCCCCN(CCC12CC3CC(CC(C3)C1)C2)C(=O)CCSCc1ccncc1]

11

2-[2-(4-pyridyl)ethylthio]acetic acid N-[2-(1-adamantyl)ethyl]-N-pentylamide

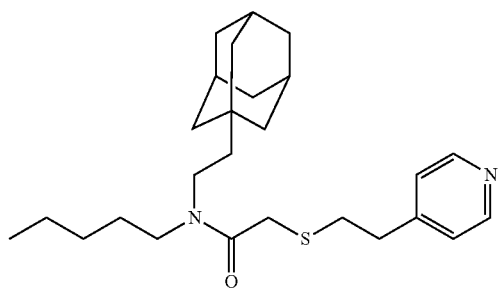 [SMILES: CCCCCN(CCC12CC3CC(CC(C3)C1)C2)C(=O)CSCCc1ccncc1]

6-(4-pyridyl)caproic acid N-[2-(1-adamantyl)ethyl]-N-pentylamide

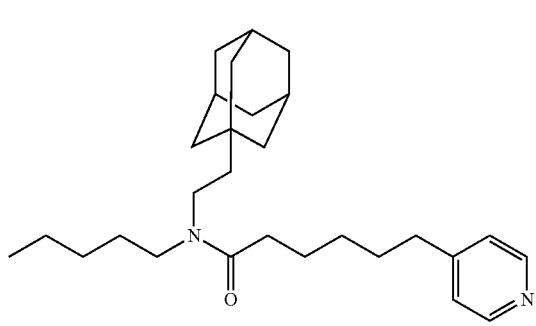 [SMILES: CCCCCN(CCC12CC3CC(CC(C3)C1)C2)C(=O)CCCCCc1ccncc1]

cis-1-[2-(1-adamantyl)ethyl]-1-pentyl-3-[2-(4-pyridyl)cyclopropylmethyl]urea

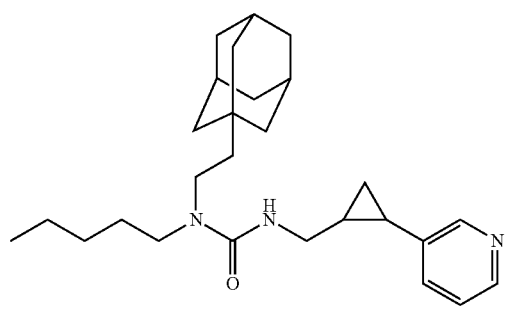 [SMILES: CCCCCN(CCC12CC3CC(CC(C3)C1)C2)C(=O)NCC1CC1c1cccnc1]

12

1-[2-(1-adamantyl)ethyl]-3-[2-methyl-3-(4-pyridyl)propyl]-1-pentylurea

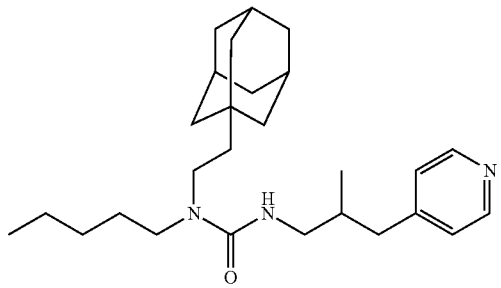 [SMILES: CCCCCN(CCC12CC3CC(CC(C3)C1)C2)C(=O)NCC(C)Cc1ccncc1]

1-[2-(1-adamantyl)ethyl]-1-[2-[N-(t-butoxycarbonyl)-N-methylamino]ethyl]-3-[2-methyl-3-(4-pyridyl)propyl]urea

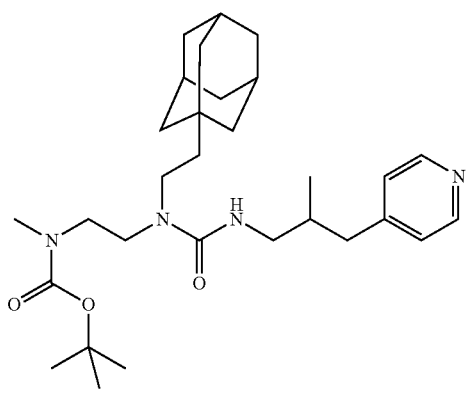 [SMILES: CC(CNC(=O)N(CCN(C)C(=O)OC(C)(C)C)CCC12CC3CC(CC(C3)C1)C2)Cc1ccncc1]

(E)-1-[2-(1-adamantyl)ethyl]-1-pentyl-3-[3-(4-pyridyl)-2-propenyl]urea

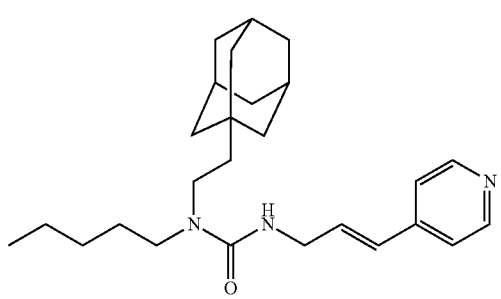 [SMILES: CCCCCN(CCC12CC3CC(CC(C3)C1)C2)C(=O)NC/C=C/c1ccncc1]

(+)-1-[2-(1-adamantyl)ethyl]-3-[2-methyl-3-(4-pyridyl)propyl]-1-pentylurea

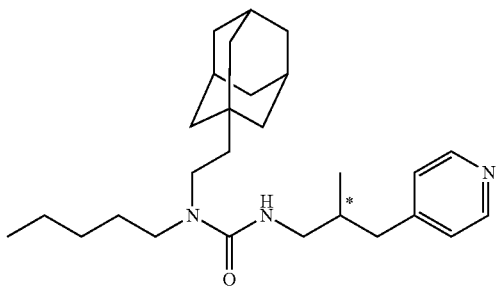 [SMILES: CCCCCN(CCC12CC3CC(CC(C3)C1)C2)C(=O)NCC(C)Cc1ccncc1]

The subject compound is most preferably 1-[2-(1-adamantyl)ethyl]-1-pentyl-3-[3-(4-pyridyl)propyl]urea (which may be hereinafter referred to as a "compound A").

The subject compound may be produced, for example, according to the method described in JP-A-2002-53555.

Examples of the lipophilic substance in the invention include a fatty acid, a fatty acid salt, an ester of a fatty acid and a monohydric alcohol, and an ester of a fatty acid and a polyhydric alcohol. These are widely distributed as a component of an oil and fat, a lipid and the like in the natural animal and plant world, and the examples of the lipophilic substance of the invention also include a natural oil and fat and a natural lipid containing the component.

The fatty acid, the fatty acid salt, the ester of a fatty acid and a monohydric alcohol, the ester of a fatty acid and a polyhydric alcohol, and the natural oil and fat and natural lipid containing the component, as the lipophilic substance in the invention will be described below.

The fatty acid represents a saturated or unsaturated medium-chain fatty acid having from 6 to 13 carbon atoms and a saturated or unsaturated long-chain fatty acid having from 14 to 22 carbon atoms. Examples of the fatty acid include, as the medium-chain fatty acid, caproic acid, enanthic acid, caprylic acid, isooctanoic acid, pelargonic acid, capric acid, dimethyloctanoic acid, neodecanoic acid, undecanoic acid (undecylic acid), undecylenic acid and lauric acid, and also include, as the long-chain fatty acid, myristic acid, pentadecanoic acid, palmitic acid, palmitoleic acid, margaric acid, stearic acid, isostearic acid, oleic acid, linoleic acid, linolenic acid, ricinoleic acid, nonadecanoic acid, eicosenoic acid, arachidonic acid and behenic acid.

The fatty acid salt includes alkali metal salts (such as sodium salts and potassium salts) and alkaline earth metal salts (such as magnesium salts and calcium salts) of the aforementioned fatty acids. Examples of the fatty acid salt include sodium caproate, sodium caprylate, sodium myristate and sodium palmitate.

The ester of a fatty acid and a monohydric alcohol represents esters of the aforementioned fatty acids and a monohydric alcohol, such as methanol, ethanol, isopropanol, butanol, hexyl alcohol, decyl alcohol, cetyl alcohol, isocetyl alcohol, oleyl alcohol, octyldodecyl alcohol, isostearyl alcohol and hexyldecyl alcohol. Examples of the ester of a fatty acid and a monohydric alcohol include ethyl linoleate, ethyl oleate, isopropyl myristate, isopropyl palmitate, isopropyl isostearate, isopropyl linoleate, butyl myristate, butyl stearate, hexyl laurate, decyl oleate, cetyl isooctanoate, isocetyl myristate, isocetyl isostearate, oleyl oleate, octyldodecyl myristate, octyldodecyl neodecanoate, isostearyl palmitate and hexyldecyl dimethyloctanoate.

The ester of a fatty acid and a polyhydric alcohol represents an ester of the aforementioned fatty acids and a polyhydric alcohol. The polyhydric alcohol herein may be any compound that has two or more alcoholic hydroxy groups in the molecule without particular limitation, and examples thereof include ethylene glycol, propylene glycol and glycerin. Accordingly, examples of the ester of a fatty acid and a polyhydric alcohol include an ethylene glycol fatty acid ester, a propylene glycol fatty acid ester and a glycerin fatty acid ester.

The ester of a fatty acid and a polyhydric alcohol is formed with an ester bond between the hydroxy group of the polyhydric alcohol and one or more fatty acid, and in the case where plural hydroxy groups form ester bonds with fatty acids, the fatty acids may be the same as or different from each other. A polymer, such as a polyethylene glycol fatty acid ester and a polyglycerin fatty acid ester, is not included in the ester of a fatty acid and a polyhydric alcohol in the invention.

Specific examples of the ethylene glycol fatty acid ester particularly include ethylene glycol monocaprylate, ethylene glycol dicaprylate, ethylene glycol monoisooctanoate and ethylene glycol diisooctanoate.

Specific examples of the propylene glycol fatty acid ester particularly include propylene glycol monocaprylate (such as product name: Sefsol 218, produced by Nikko Chemicals Co., Ltd.), propylene glycol dicaprylate (such as product name: Sefsol 228, produced by Nikko Chemicals Co., Ltd.), propylene glycol caprylate (such as product name: CAPRYOL (registered trade name) PGMC, produced by Gattefosse Corporation), propylene glycol monocaprate, propylene glycol dicaprate (such as product name: PDD, produced by Nikko Chemicals Co., Ltd.), propylene glycol monolaurate (such as product name: Lauroglycol (registered trade name) 90, produced by Gattefosse Corporation), propylene glycol dilaurate, propylene glycol laurate (such as product name: Lauroglycol (registered trade name) FCC, produced by Gattefosse Corporation), propylene glycol monoisooctanoate (such as product name: Sefsol 2126, produced by Nikko Chemicals Co., Ltd.), propylene glycol diisooctanoate (such as product name: Sefsol 2226, produced by Nikko Chemicals Co., Ltd.), propylene glycol myristate, propylene glycol monostearate, propylene glycol distearate, propylene glycol isostearate (Corum 5083, produced by Corum, Inc.), propylene glycol oleate (such as product name: Lutrol (registered trade name) OP2000, produced by BASF SE), propylene glycol ricinoleate, propylene glycol caprylate/caprate, and propylene glycol dicaprylate/dicaprate (such as product name: Captex 200, produced by Abitec Corporation).

Specific examples of the glycerin fatty acid ester include glycerol monocaprylate (such as product name: HOMOTEX PT, produced by Kao Corporation, and IMWITOR 308, produced by Sasol, Ltd.), glycerol mono/dicaprylate (such as product name: IMWITOR 988, produced by Sasol, Ltd., and Capmul (registered trade name) MCM C8, produced by Abitec Corporation), glyceryl caprylate, glyceryl caprate (such as product name: Capmul (registered trade name) MCM C10, produced by Abitec Corporation), caprylic/capric glyceride (such as product name: IMWITOR 742, produced by Sasol, Ltd.), glyceryl monolaurate (such as product name: IMWITOR 312, produced by Sasol, Ltd.), glyceryl monomyristate, glyceryl monostearate (such as product name: EMALEX GMS-50, produced by Nihon Emulsion Co., Ltd.), glyceryl palmitate (such as product name: EMALEX GMS-P, produced by Nihon Emulsion Co., Ltd.), glyceryl monostearate/palmitate, glyceryl palmitic/stearic, glyceryl monooleate (such as product name: MGO, produced by Nikko Chemicals Co., Ltd.), glyceryl oleate (such as product name: Capmul (registered trade name) GMO, produced by Abitec Corporation), glyceryl mono/dioleate, glyceryl monolinoleate, glycerol monooleate/linoleate, glyceryl ricinoleate (such as product name: Softigen 701, produced by Sasol, Ltd.), glyceryl tricaproate, glyceryl tricaprylate, glyceryl tricaprate (such as product name: Captex 1000, produced by Abitec Corporation), glyceryl triundecanoate (such as product name: Captex 8227, produced by Abitec Corporation), glyceryl trilaurate, glyceryl trioleate, glyceryl trilinoleate, glyceryl trilinolenate, caprylic/capric triglyceride (such as product name: MIGLYOL (registered trade name) 810, produced by Sasol, Ltd.), glyceryl tricaprylate/caprate/laurate (such as product name: MIGLYOL (registered trade name) 818, produced by Sasol, Ltd.), glyceryl tricaprylate/caprate/linoleate (such as product name: Captex 810, produced by Abitec Corporation), glyceryl tricaprylate/caprate/stearate, and caprylic/capric/myristic/stearic triglyceride (such as product name: SOFTISAN 378, produced by Sasol, Ltd.).

Examples of the natural oil and fat and natural lipid containing the lipophilic component include almond oil, babassu oil, borage oil, black currant seed oil, canola oil, castor oil, coconut oil, corn oil, cotton seed oil, oenothera oil, grape seed oil, wild bean oil, mustard seed oil, olive oil, palm oil, palm kernel oil, peanut oil, rapeseed oil, safflower oil, sesame oil, shark liver oil, soybean oil, sunflower seed oil, hydrogenated castor oil, hydrogenated coconut oil, hydrogenated palm oil and hydrogenated soybean oil.

The lipophilic substance in the invention is preferably an ester of a fatty acid and a polyhydric alcohol, more preferably a propylene glycol fatty acid ester or a glycerin fatty acid ester, further preferably propylene glycol monocaprylate, propylene glycol dicaprylate, propylene glycol caprylate, glycerol monocaprylate, glycerol mono/dicaprylate, glyceryl caprylate or glyceryl tricaprylate, and particularly preferably propylene glycol monocaprylate, glycerol monocaprylate or glycerol mono/dicaprylate.

The lipophilic substance in the invention is most preferably propylene glycol monocaprylate.

These lipophilic substances do not have a single fatty acid composition since they are generally produced with a raw material derived from animals or plants, but these materials are favorably used for the objects of the invention. In the invention, the lipophilic substance may be used solely or as a mixture of two or more kinds thereof.

The mixed amount (mixed ratio) of the lipophilic substance in the composition of the invention may be appropriately controlled depending on the compound, and is preferably from 0.01 to 100, more preferably from 0.1 to 20, and particularly preferably from 1 to 10, in terms of weight ratio with respect to the subject compound.

The composition of the invention may further comprise a solubilizer and/or a surfactant.

The solubilizer in the invention may be any material that enhances the solubility of the subject compound without particular limitation, and examples thereof include an alcohol, an amide, an ester and other solubilizers. In the invention, however, an ester of a fatty acid and a monohydric alcohol or a polyhydric alcohol is not included in the ester as the solubilizer.

The monohydric alcohol, polyhydric alcohol, amide, ester and other solubilizers in the invention will be described below.

Specific examples of the monohydric alcohol and polyhydric alcohol particularly include ethanol, dehydrated ethanol, isopropanol, dehydrated isopropanol, butanol, dehydrated butanol, benzyl alcohol, dehydrated benzyl alcohol, ethylene glycol, dehydrated ethylene glycol, propylene glycol, dehydrated propylene glycol, butanediol, glycerol, pentaerythritol, sorbitol, mannitol, transcutol, dimethylisosorbide, polyethylene glycol, polypropylene glycol, polyvinyl alcohol, hydroxypropyl methyl cellulose, other cellulose derivatives, cyclodextrin, and a cyclodextrin derivative.

Specific examples of the amide include 2-pyrrolidone, ε-caprolactam, an N-alkylpyrrolidone (including N-methylpyrrolidone), an N-hydroxyalkylpyrrolidone, an N-alkylpiperidone, an N-alkylcaprolactam, dimethylacetamide and polyvinylpyrrolidone.

Specific examples of the ester include ethyl propionate, tributyl citrate, acetyltriethyl citrate, acetyltributyl citrate, triethyl citrate, ethyl oleate, ethyl caprylate, ethyl butyrate and triacetin.

Examples of the other solubilizers particularly include dimethylisosorbide, monooctane and acetone.

The solubilizer in the invention is preferably a monohydric alcohol or a polyhydric alcohol, and particularly preferably a monohydric alcohol.

In the invention, the solubilizer may be used solely or as a mixture of two or more kinds thereof.

In the case where the solubilizer is added to the composition of the invention, the mixed amount (mixed ratio) of the solubilizer may be appropriately controlled depending on the compound, and is preferably from 0.001 to 10, more preferably from 0.005 to 5, and particularly preferably from 0.01 to 2, in terms of weight ratio with respect to the subject compound.

The surfactant in the invention may be any material that enhances the solubility of the subject compound without particular limitation, and examples thereof include an ionic surfactant, such as a bile salt, a phospholipid and a cationic surfactant, a nonionic surfactant, such as a polyoxyethylene alkyl ether, a polyoxyethylene sorbitan fatty acid ester, polyoxyethylene castor oil, polyoxyethylene hydrogenated castor oil, a polyethylene glycol fatty acid ester, a sorbitan fatty acid ester, a sucrose fatty acid ester, a polyoxyethylene-polyoxypropylene copolymer, a polyglycerin fatty acid ester and saturated polyglycolated glyceride, and other surfactants.

The bile salt, phospholipid, cationic surfactant, polyoxyethylene alkyl ether, polyoxyethylene sorbitan fatty acid ester, polyoxyethylene castor oil, polyoxyethylene hydrogenated castor oil, polyethylene glycol fatty acid ester, sorbitan fatty acid ester, sucrose fatty acid ester, polyoxyethylene-polyoxypropylene copolymer, polyglycerin fatty acid ester, saturated polyglycolated glyceride, and other surfactants, as the surfactant in the invention will be described below.

Specific examples of the bile salt particularly include sodium cholate, sodium taurocholate and sodium glycocholate.

Specific examples of the phospholipid particularly include purified egg-yolk lecithin and purified soybean lecithin.

Specific examples of the cationic surfactant particularly include lauroylcarnitine, palmitoylcarnitine and myristoylcarnitine.

Specific examples of the polyoxyethylene alkyl ether particularly include polyoxyethylene oleyl ether, polyoxyethylene stearyl ether, polyoxyethylene cetyl ether and polyoxyethylene lauryl ether.

Specific examples of the polyoxyethylene sorbitan fatty acid ester particularly include polysorbate 20 (such as product name: CRILLET 1 HP, produced by Croda International PLC), polysorbate 60 (such as product name: CRILLET 3 NF, produced by Croda International PLC), polysorbate 80 (such as product name: CRILLET 4 HP, produced by Croda International PLC) and polysorbate 120 (such as product name: CRILLET 6, produced by Croda International PLC).

Specific examples of the polyoxyethylene sorbitol fatty acid ester particularly include polyoxyethylene sorbit tetraoleate, polyoxyethylene sorbit hexastearate and polyoxyethylene sorbit monolaurate.

Specific examples of the polyoxyethylene castor oil particularly include PEG 20 castor oil (such as product name: EMALEX C-20, produced by Nihon Emulsion Co., Ltd.), PEG 30 castor oil (such as product name: EMALEX C-30, produced by Nihon Emulsion Co., Ltd.), polyoxyl 35 castor oil (such as product name: Cremophor EL, produced by BASF SE), PEG 40 castor oil (such as product name: EMALEX C-40, produced by Nihon Emulsion Co., Ltd.) and PEG 50 castor oil (such as product name: EMALEX C-50, produced by Nihon Emulsion Co., Ltd.).

Specific examples of the polyoxyethylene hydrogenated castor oil particularly include polyoxyethylene hydrogenated castor oil 5 (such as product name: HCO-5, produced by Nikko Chemicals Co., Ltd.), polyoxyethylene hydrogenated castor oil 10 (such as product name: HCO-10, produced by Nikko Chemicals Co., Ltd.), polyoxyethylene hydrogenated castor oil 20 (such as product name: HCO-20, produced by Nikko Chemicals Co., Ltd.), polyoxyethylene hydrogenated castor oil 30 (such as product name: HCO-30, produced by Nikko Chemicals Co., Ltd.), polyoxyethylene hydrogenated castor oil 40 (such as product name: HCO-40, produced by Nikko Chemicals Co., Ltd.), polyoxyethylene hydrogenated castor oil 50 (such as product name: HCO-50, produced by Nikko Chemicals Co., Ltd.), polyoxyethylene hydrogenated castor oil 60 (such as product name: HCO-60, produced by Nikko Chemicals Co., Ltd.), polyoxyethylene hydrogenated castor oil 80 (such as product name: HCO-80, produced by Nikko Chemicals Co., Ltd.) and polyoxyethylene hydrogenated castor oil 100 (such as product name: HCO-100, produced by Nikko Chemicals Co., Ltd.).

Specific examples of the polyethylene glycol fatty acid ester particularly include polyethylene glycol monolaurate (such as product name: EMALEX PEL-12, produced by Nihon Emulsion Co., Ltd.), polyethylene glycol monooleate (such as product name: MYO-10V, produced by Nikko Chemicals Co., Ltd.) and polyethylene glycol monostearate. Specific examples of the polyethylene glycol monostearate include PEG 10 stearate (such as product name: MYS-10V, produced by Nikko Chemicals Co., Ltd.), PEG 25 stearate (such as product name: MYS-25V, produced by Nikko Chemicals Co., Ltd.), PEG 40 stearate (such as product name: MYS-40V, produced by Nikko Chemicals Co., Ltd.), PEG 45 stearate (such as product name: MYS-45V, produced by Nikko Chemicals Co., Ltd.) and PEG 55 stearate (such as product name: MYS-55V, produced by Nikko Chemicals Co., Ltd.).

Specific examples of the sucrose fatty acid ester include sucrose monolaurate, sucrose dilaurate, sucrose monopalmitate, sucrose dipalmitate, sucrose monostearate, sucrose distearate, sucrose monooleate and sucrose dioleate.

Specific examples of the polyoxyethylene-polyoxypropylene copolymer include polyoxyethylene (150) polyoxypropylene (35) glycol (such as product name: Pluronic F-87, produced by BASF SE), polyoxyethylene (200) polyoxypropylene (70) glycol (such as product name: Pluronic F-127, produced by BASF SE), polyoxyethylene (160) polyoxypropylene (30) glycol (which may also be referred to as Poloxamer 188) (such as product name: Pluronic F-68, produced by BASF SE), polyoxyethylene (20) polyoxypropylene (20) glycol (such as product name: Pluronic L-44, produced by BASF SE) and polyoxyethylene (105) polyoxypropylene (5) glycol (which may also be referred to as PEP-101).

Specific examples of the polyglycerin fatty acid ester include diglyceryl monostearate (such as product name: DGMS, produced by Nikko Chemicals Co., Ltd.), diglyceryl monooleate (such as product name: DGMO-CV, produced by Nikko Chemicals Co., Ltd.), diglyceryl monoisostearate (such as product name: DGMIS, produced by Nikko Chemicals Co., Ltd.), decaglyceryl monolaurate (such as product name: Decaglyn 1-L, produced by Nikko Chemicals Co., Ltd.) and decaglyceryl monooleate (such as product name: Decaglyn 1-OV, produced by Nikko Chemicals Co., Ltd.).

Specific examples of the saturated polyglycolated glyceride include Gelucire 44/14, Gelucire 50/13 and Gelucire 53/10 (all of which are product names).

Specific examples of the other surfactants particularly include d-α-tocopherylpolyethylene glycol 1000 (product name: Vitamin E TPGS NF, produced by Eastman Chemical Company).

The surfactant in the invention is preferably a polyoxyethylene sorbitan fatty acid ester, polyoxyethylene castor oil, polyoxyethylene hydrogenated castor oil, a polyglycerin fatty acid ester or d-α-tocopherylpolyethylene glycol 1000, and particularly preferably polyoxyethylene hydrogenated castor oil.

In the invention, the surfactant may be used solely or as a mixture of two or more kinds thereof.

In the case where the surfactant is added to the composition of the invention, the mixed amount (mixed ratio) of the surfactant may be appropriately controlled depending on the compound, and is preferably from 0.001 to 20, more preferably from 0.005 to 10, and particularly preferably from 0.01 to 5, in terms of weight ratio with respect to the subject compound.

A pharmaceutical formulation of the subject compound may be prepared as a single formulation or a mixed formulation by adding a pharmaceutically acceptable additive thereto according to the ordinarily employed techniques.

The composition of the invention may be formed into a capsule, a powder, a granule, a pill, a tablet or a liquid formulation, and a capsule is particularly preferred.

The composition of the invention is in the form of a liquid, a semi-solid or a solid, and may be used as a capsule, a powder, a granule, a pill, a tablet or a liquid formulation, as it is or after appropriately adding thereto an excipient, such as lactose, glucose, D-mannitol, anhydrous calcium hydrogen phosphate, starch and sucrose; a disintegrating agent, such as carboxymethyl cellulose, carboxymethyl cellulose calcium, croscarmellose sodium, crospovidone, starch, partially gelatinized starch and low substitution degree hydroxypropyl cellulose; a binder, such as hydroxypropyl cellulose, ethyl cellulose, gum arabic, starch, partially gelatinized starch, polyvinylpyrrolidone and polyvinyl alcohol; a lubricant, such as magnesium stearate, calcium stearate, talc, hydrated silicon dioxide and hydrogenated oil; a coating agent, such as purified sucrose, hydroxypropyl methyl cellulose, hydroxypropyl cellulose, methyl cellulose, ethyl cellulose and polyvinylpyrrolidone; a flavoring agent, such as citric acid, aspartame, ascorbic acid and menthol; and the like.

In the invention, the language "to improve intestinal absorption" means that higher intestinal absorption of the subject compound is obtained upon administering the subject compound to a patient in the form of a solid formulation, such as a tablet, a liquid formulation (including a capsule form) or the like, as compared to the case where a lipophilic substance is not contained in the vehicle of the formulations, thereby resulting in high bioavailability. The term "intestinal" herein means small intestines (such as jejunum and duodenum), large intestines (such as colon and rectum) and the like.

Examples are shown below, but the examples are for better comprehension of the invention and do not restrict the scope of the invention.

EXAMPLE

Examples 1 to 6 and Comparative Example

The entry of the subject compound into the blood upon administering the composition of the invention to a duodenum of a rat was investigated.

Example 1

50 parts by weight of the compound A was dissolved in 150 parts by weight of glycerol mono/dicaprylate (IMWITOR 988, produced by Sasol, Ltd., which was the same in the examples) to prepare a sample. The sample in an amount corresponding to 1 mg of the compound A was administered to a duodenum of a non-fasting rat (SD male rat, n=3) by using an injection syringe with a needle. The blood was collected at 0.25, 0.5, 1, 2, 4 and 6 hours after the administration, and the concentration of the compound A in the resulting blood plasma was measured with a high-performance liquid chromatography mass spectrometer (LC-MS/MS). The area under the plasma concentration-time curve (AUC) and the maximum plasma concentration (Cmax) were calculated from the resulting transition of the plasma concentration of the compound A.

Example 2

50 parts by weight of the compound A was dissolved in 100 parts by weight of glycerol mono/dicaprylate, 25 parts by weight of polyoxyethylene hydrogenated castor oil 60 (HCO-60, produced by Nikko Chemicals Co., Ltd., which was the same in the examples) and 25 parts by weight of dehydrated ethanol to prepare a sample. The sample in an amount corresponding to 1 mg of the compound A was administered to a duodenum of a rat, and then the transition of the plasma concentration was measured, from which AUC and Cmax were obtained, in the same manner as in Example 1.

Example 3

50 parts by weight of the compound A was dissolved in 227 parts by weight of glycerol mono/dicaprylate, 113 parts by weight of polyoxyethylene hydrogenated castor oil 60 and 30 parts by weight of dehydrated ethanol to prepare a sample. The sample in an amount corresponding to 1 mg of the compound A was administered to a duodenum of a rat, and then the transition of the plasma concentration was measured, from which AUC and Cmax were obtained, in the same manner as in Example 1.

Example 4

50 parts by weight of the compound A was dissolved in 150 parts by weight of propylene glycol monocaprylate (Sefsol 218, produced by Nikko Chemicals Co., Ltd., which was the same in the examples) to prepare a sample. The sample in an amount corresponding to 1 mg of the compound A was administered to a duodenum of a rat, and then the transition of the plasma concentration was measured, from which AUC and Cmax were obtained, in the same manner as in Example 1.

Example 5

50 parts by weight of the compound A was dissolved in 148 parts by weight of propylene glycol monocaprylate and 2 parts by weight of dehydrated ethanol to prepare a sample. The sample in an amount corresponding to 1 mg of the compound A was administered to a duodenum of a rat, and then the transition of the plasma concentration was measured, from which AUC and Cmax were obtained, in the same manner as in Example 1.

Example 6

50 parts by weight of the compound A was dissolved in 237 parts by weight of glycerol monocaprylate (HOMOTEX PT, produced by Kao Corporation, which was the same in the examples), 118 parts by weight of decaglyceryl monolaurate (Decaglyn 1-L, produced by Nikko Chemicals Co., Ltd.) and parts by weight of dehydrated ethanol to prepare a sample. The sample in an amount corresponding to 1 mg of the compound A was administered to a duodenum of a rat, and then the transition of the plasma concentration was measured, from which AUC and Cmax were obtained, in the same manner as in Example 1.

Comparative Example 10 parts by weight of the compound A was suspended in 1,000 parts by weight of the dissolution test liquid 1 according to the Pharmacopoeia of Japan, 15th edition (which is hereinafter referred to as a "dissolution test liquid 1") to prepare a sample. The sample in an amount corresponding to 1 mg of the compound A was administered to a duodenum of a rat, and then the transition of the plasma concentration was measured, from which AUC and Cmax were obtained, in the same manner as in Example 1. The dissolution test liquid 1 can be obtained by dissolving 2.0 g of sodium chloride and 7.0 mL of hydrochloric acid in water to make 1,000 mL.

The mixing ratios of the compositions of Examples 1 to 6 and Comparative Example, and the AUC and Cmax thus calculated are shown in Table 1.

TABLE 1

| | | Comparative Example | Example 1 | Example 2 | Example 3 | Example 4 | Example 5 | Example 6 |
|---|---|---|---|---|---|---|---|---|
| Mixing ratio (% by weight) | Compound A | 1.0 | 25.0 | 25.0 | 11.9 | 25.0 | 25.0 | 11.9 |
| | glycerol mono/dicaprylate | | 75.0 | 50.0 | 54.0 | | | |
| | glycerol monocaprylate | | | | | | | 56.4 |
| | propylene glycol monocaprylate | | | | | 75.0 | 74.0 | |

TABLE 1-continued

|  | Comparative Example | Example 1 | Example 2 | Example 3 | Example 4 | Example 5 | Example 6 |
|---|---|---|---|---|---|---|---|
| polyoxyethylene hydrogenated castor oil 60 |  |  | 12.5 | 27.0 |  |  |  |
| decaglyceryl monolaurate |  |  |  |  |  |  | 28.1 |
| dehydrated ethanol |  |  | 12.5 | 7.1 |  | 1.0 | 3.6 |
| dissolution test liquid 1 | 99.0 |  |  |  |  |  |  |
| AUC (hr · ng/mL) | 49.1 | 60.1 | 90.7 | 116 | 78.4 | 146 | 84.0 |
| Cmax (ng/mL) | 16.4 | 21.1 | 40.0 | 86.9 | 39.0 | 53.9 | 37.3 |

As apparent from the comparison between Comparative Example and Examples 1 and 4 in Table 1, it was demonstrated that the AUC and Cmax in the case where the compound A (corresponding to 1 mg) dissolved in glycerol mono/dicaprylate or propylene glycol monocaprylate was administered to a duodenum were larger than those in the case where the compound A was administered as a suspension liquid in the dissolution test liquid 1 (which simulated the state where an ordinary solid formulation, such as a tablet, was disintegrated in a gastric cavity). In particular, propylene glycol monocaprylate provided high AUC and Cmax as compared to glycerol mono/dicaprylate, which was a lipophilic substance of the same kind. This is a startling result.

Furthermore, as apparent from the comparison of Examples 1 to 5, it was confirmed that the addition of dehydrated ethanol as a solubilizer and/or polyoxyethylene hydrogenated castor oil or decaglyceryl monolaurate as a surfactant further enhanced the AUC and Cmax.

As shown in Example 6, it was observed that the use of glycerol monocaprylate as the other lipophilic substance provided the similar tendency.

Accordingly, it is considered that the composition comprising the subject compound, which is represented by the compound A, and the lipophilic substance, which is represented by propylene glycol monocaprylate, glycerol mono/dicaprylate and glycerol monocaprylate, considerably improves the intestinal absorption of the subject compound.

Examples 7 to 12

The entry of the subject compound into the blood upon administering the composition of the invention to a jejunum of a rat was investigated.

Example 7

50 parts by weight of the compound A was dissolved in 120 parts by weight of propylene glycol monocaprylate, 5 parts by weight of polyoxyethylene hydrogenated castor oil 60 and 25 parts by weight of dehydrated ethanol to prepare a sample. The sample in an amount corresponding to 1 mg of the compound A was administered to a jejunum of a rat (SD male rat, n=3) fasted overnight by using an injection syringe with a needle. The blood was collected at 0.25, 0.5, 1, 2, 4 and 6 hours after the administration, and the concentration of the compound A in the resulting blood plasma was measured with a high-performance liquid chromatography mass spectrometer (LC-MS/MS). The AUC and Cmax were calculated from the resulting transition of the plasma concentration of the compound A.

Example 8

50 parts by weight of the compound A was dissolved in 100 parts by weight of propylene glycol monocaprylate, 25 parts by weight of polyoxyethylene hydrogenated castor oil 60 and 25 parts by weight of dehydrated ethanol to prepare a sample. The sample in an amount corresponding to 1 mg of the compound A was administered to a jejunum of a rat, and then the transition of the plasma concentration was measured, from which AUC and Cmax were obtained, in the same manner as in Example 7.

Example 9

50 parts by weight of the compound A was dissolved in 100 parts by weight of propylene glycol monocaprylate, 25 parts by weight of polysorbate 80 (CRILLET 4 HP, produced by Croda International PLC, which was the same in the examples) and 25 parts by weight of dehydrated ethanol to prepare a sample. The sample in an amount corresponding to 1 mg of the compound A was administered to a jejunum of a rat, and then the transition of the plasma concentration was measured, from which AUC and Cmax were obtained, in the same manner as in Example 7.

Example 10

50 parts by weight of the compound A was dissolved in 100 parts by weight of propylene glycol monocaprylate, 25 parts by weight of polyoxyl 35 castor oil (Cremophor EL, produced by BASF SE) and 25 parts by weight of dehydrated ethanol to prepare a sample. The sample in an amount corresponding to 1 mg of the compound A was administered to a jejunum of a rat, and then the transition of the plasma concentration was measured, from which AUC and Cmax were obtained, in the same manner as in Example 7.

Example 11

50 parts by weight of the compound A was dissolved in 125 parts by weight of glycerol monocaprylate and 25 parts by weight of dehydrated ethanol to prepare a sample. The sample in an amount corresponding to 1 mg of the compound A was administered to a jejunum of a rat, and then the transition of the plasma concentration was measured, from which AUC and Cmax were obtained, in the same manner as in Example 7.

Example 12

50 parts by weight of the compound A was dissolved in 100 parts by weight of glycerol monocaprylate, 25 parts by weight of polyoxyl 35 castor oil and 25 parts by weight of dehydrated ethanol to prepare a sample. The sample in an amount corresponding to 1 mg of the compound A was administered to a jejunum of a rat, and then the transition of the plasma concentration was measured, from which AUC and Cmax were obtained, in the same manner as in Example 7.

The mixing ratios of the compositions of Examples 7 to 12 and the AUC and Cmax thus calculated are shown in Table 2.

TABLE 2

| | | Example 7 | Example 8 | Example 9 | Example 10 | Example 11 | Example 12 |
|---|---|---|---|---|---|---|---|
| Mixing ratio (% by weight) | Compound A | 25.0 | 25.0 | 25.0 | 25.0 | 25.0 | 25.0 |
| | propylene glycol monocaprylate | 60.0 | 50.0 | 50.0 | 50.0 | | |
| | glycerol monocaprylate | | | | | 62.5 | 50.0 |
| | polyoxyethylene hydrogenated castor oil 60 | 2.5 | 12.5 | | | | |
| | polysorbate 80 | | | 12.5 | | | |
| | polyoxyl 35 castor oil | | | | 12.5 | | 12.5 |
| | dehydrated ethanol | 12.5 | 12.5 | 12.5 | 12.5 | 12.5 | 12.5 |
| | AUC (hr · ng/mL) | 65.2 | 94.1 | 67.9 | 75.5 | 54.4 | 69.4 |
| | Cmax (ng/mL) | 32.6 | 48.4 | 27.8 | 29.8 | 21.8 | 36.2 |

As apparent from the results shown in Table 2, favorable AUC and Cmax, which were similar to the case of administration to a duodenum, were also obtained in the case where the compound A (corresponding to 1 mg) dissolved in propylene glycol monocaprylate or glycerol monocaprylate was administered to a jejunum.

Accordingly, it is considered that the composition containing the subject compound, which is represented by the compound A, and the lipophilic substance, which is represented by propylene glycol monocaprylate and glycerol monocaprylate, considerably improves the intestinal absorption of the subject compound.

Examples 13 to 15

The entry of the subject compound into the blood upon orally administering the composition of the invention charged in a capsule to a dog was investigated.

Example 13

50 parts by weight of the compound A was dissolved in 227 parts by weight of glycerol mono/dicaprylate, 113 parts by weight of polyoxyethylene hydrogenated castor oil 60 and 30 parts by weight of dehydrated ethanol to prepare a sample. The sample in an amount corresponding to 20 mg of the compound A was charged in a gelatin hard capsule (Qualicaps Capsule #1), and then orally administered to a dog (male beagle dog, n=1) fasted overnight. The blood was collected at 0.5, 1, 2, 4, 6, 8 and 24 hours after the administration, and the concentration of the compound A in the resulting blood plasma was measured with a high-performance liquid chromatography mass spectrometer (LC-MS/MS).

The AUC and Cmax were calculated from the resulting transition of the plasma concentration of the compound A.

Example 14

75 parts by weight of the compound A was dissolved in 203 parts by weight of glycerol mono/dicaprylate, 102 parts by weight of polyoxyethylene hydrogenated castor oil 60 and 40 parts by weight of dehydrated ethanol to prepare a sample. The sample in an amount corresponding to 20 mg of the compound A was charged in a capsule and orally administered to a dog, and then the transition of the plasma concentration was measured, from which AUC and Cmax were obtained, in the same manner as in Example 13.

Example 15

50 parts by weight of the compound A was dissolved in 237 parts by weight of glycerol monocaprylate, 118 parts by weight of decaglyceryl monolaurate and 15 parts by weight of dehydrated ethanol to prepare a sample. The sample in an amount corresponding to 20 mg of the compound A was charged in a capsule and orally administered to a dog, and then the transition of the plasma concentration was measured, from which AUC and Cmax were obtained, in the same manner as in Example 13.

The AUC and Cmax thus obtained in Examples 13 to 15 are shown in Table 3.

TABLE 3

| | | Example 13 | Example 14 | Example 15 |
|---|---|---|---|---|
| Mixing ratio (% by weight) | Compound A | 11.9 | 17.9 | 11.9 |
| | glycerol mono/dicaprylate | 54.0 | 48.3 | |
| | glycerol monocaprylate | | | 56.4 |
| | polyoxyethylene hydrogenated castor oil 60 | 27.0 | 24.3 | |
| | decaglyceryl monolaurate | | | 28.1 |
| | dehydrated ethanol | 7.1 | 9.5 | 3.6 |
| | AUC (hr · ng/mL) | 16.0 | 28.0 | 18.3 |
| | Cmax (ng/mL) | 6.37 | 10.2 | 10.4 |

As apparent from the results shown in Table 3, favorable AUC and Cmax, which were similar to the cases of administration to a duodenum and administration to a jejunum, were also obtained in the case where the compound A (corresponding to 20 mg) dissolved in glycerol mono/dicaprylate or glycerol monocaprylate was charged in a capsule and orally administered.

Accordingly, it is considered that the composition containing the subject compound, which is represented by the compound A, and the lipophilic substance, which is represented by glycerol mono/dicaprylate and glycerol monocaprylate, considerably improves the intestinal absorption of the subject compound even in a case where the composition is charged in a capsule and orally administered.

Formulation Example

The invention will be described more specifically with reference to formulation examples, but the invention is not limited to the formulation examples.

Formulation Example 1

| Capsule (contents in 200 mg) | |
|---|---|
| Compound A | 50 mg |
| Propylene glycol monocaprylate | 148 mg |
| Dehydrated ethanol | 2 mg |

A solution obtained by mixing the aforementioned components is charged in a capsule, thereby producing a capsule. The amount of the compound A, and the kinds and/or amounts of the additives may be appropriately changed to provide an intended capsule having a different content of the compound A.

Formulation Example 2

| Liquid formulation (in 210 mg) | |
|---|---|
| Compound A | 25 mg |
| Glycerol mono/dicaprylate | 113.5 mg |
| Polyoxyethylene hydrogenated castor oil 60 | 56.5 mg |
| Dehydrated ethanol | 15 mg |

The amount of the compound A, and the kinds and/or amounts of the additives may be appropriately changed to provide an intended liquid formulation having a different content of the compound A.

Formulation Example 3

| Tablet (in 200 mg) | |
|---|---|
| Compound A | 50 mg |
| Propylene glycol monocaprylate | 2 mg |
| Lactose | 95 mg |
| Cornstarch | 40 mg |
| Carboxymethyl cellulose calcium | 6 mg |
| Hydroxypropyl cellulose | 6 mg |
| Magnesium stearate | 1 mg |

A tablet having the aforementioned formulation is coated with 3 mg of a coating agent (for example, a coating agent, such as hydroxypropyl methyl cellulose, macrogol, talc, titanium oxide or a silicone resin) to provide a target tablet. The amount of the compound A, and the kinds and/or amounts of the additives may be appropriately changed to provide an intended tablet drug having a different content of the compound A.

INDUSTRIAL APPLICABILITY

The invention is useful for providing a pharmaceutical composition that improves the intestinal absorption of the subject compound.

The invention claimed is:

1. A pharmaceutical composition comprising (a) 1-[2-(1-adamantyl)ethyl]-1-pentyl-3-[3-(4-pyridyl)propyl]urea or a salt thereof and (b) a lipophilic substance, wherein the lipophilic substance is a propylene glycol monocaprylate.

2. The composition according to claim 1, which further comprises a solubilizer and/or a surfactant.

3. A method for improving intestinal absorption of 1-[2-(1-adamantyl)ethyl]-1-pentyl-3-[3-(4-pyridyl)propyl]urea or a salt thereof, which method comprises administering to a patient a pharmaceutical composition comprising (a) 1-[2-(1-adamantyl)ethyl]-1-pentyl-3-[3-(4-pyridyl)propyl]urea and (b) a lipophilic substance, wherein the lipophilic substance is propylene glycol monocaprylate.

4. The method according to claim 3, wherein the pharmaceutical composition comprises a solubilizer and/or a surfactant.

* * * * *